United States Patent [19]

Schlager

[11] 4,193,393
[45] Mar. 18, 1980

[54] DIAGNOSTIC APPARATUS

[75] Inventor: Kenneth J. Schlager, Elm Grove, Wis.

[73] Assignee: International Bio-Medical Industries, Newport Beach, Calif.

[21] Appl. No.: 827,600

[22] Filed: Aug. 25, 1977

[51] Int. Cl.$^2$ .................................................. A61B 5/04
[52] U.S. Cl. ................................... 128/710; 128/706; 128/702
[58] Field of Search ................ 324/77 G, 77 R, 77 A, 324/78 D, 78 R, 79; 340/248 A

[56] References Cited

U.S. PATENT DOCUMENTS

| | | | |
|---|---|---|---|
| 3,431,405 | 3/1969 | Dawson | 324/77 G |
| 3,828,279 | 8/1974 | Labarber et al. | 324/78 D |
| 3,922,670 | 11/1975 | Shaw et al. | 324/78 D |
| 3,940,692 | 2/1976 | Neilson | 324/77 R |
| 3,971,994 | 7/1976 | Shepherd | 324/79 D |
| 3,990,006 | 11/1976 | Zebo | 324/78 D |

*Primary Examiner*—William E. Kamm
*Attorney, Agent, or Firm*—Andrus, Sceales, Starke & Sawall

[57] ABSTRACT

A numeric diagnostic electrocardiometer includes an A/D converter for converting an EKG signal at each of the conventional electrodes employed in EKG analysis into numbers which are stored in an assigned memory as time and amplitude signals. The waveform is divided into time segments within which the basic waveshape is known. A programmed logic array stores abnormalities within a range for each segment of the EKG waveforms. The stored samples are read into the programmed logic array and deviation of the waveform beyond that programmed produces a numeric output. The instrument may directly translate any deviation output into a readout code referenced to a suitable manual for each combination of time and sampled data. The individually stored samples may also be read out from the memory. The instrument also includes a heart rate and heart arrythmia detection units for initial analysis of the heart.

20 Claims, 8 Drawing Figures

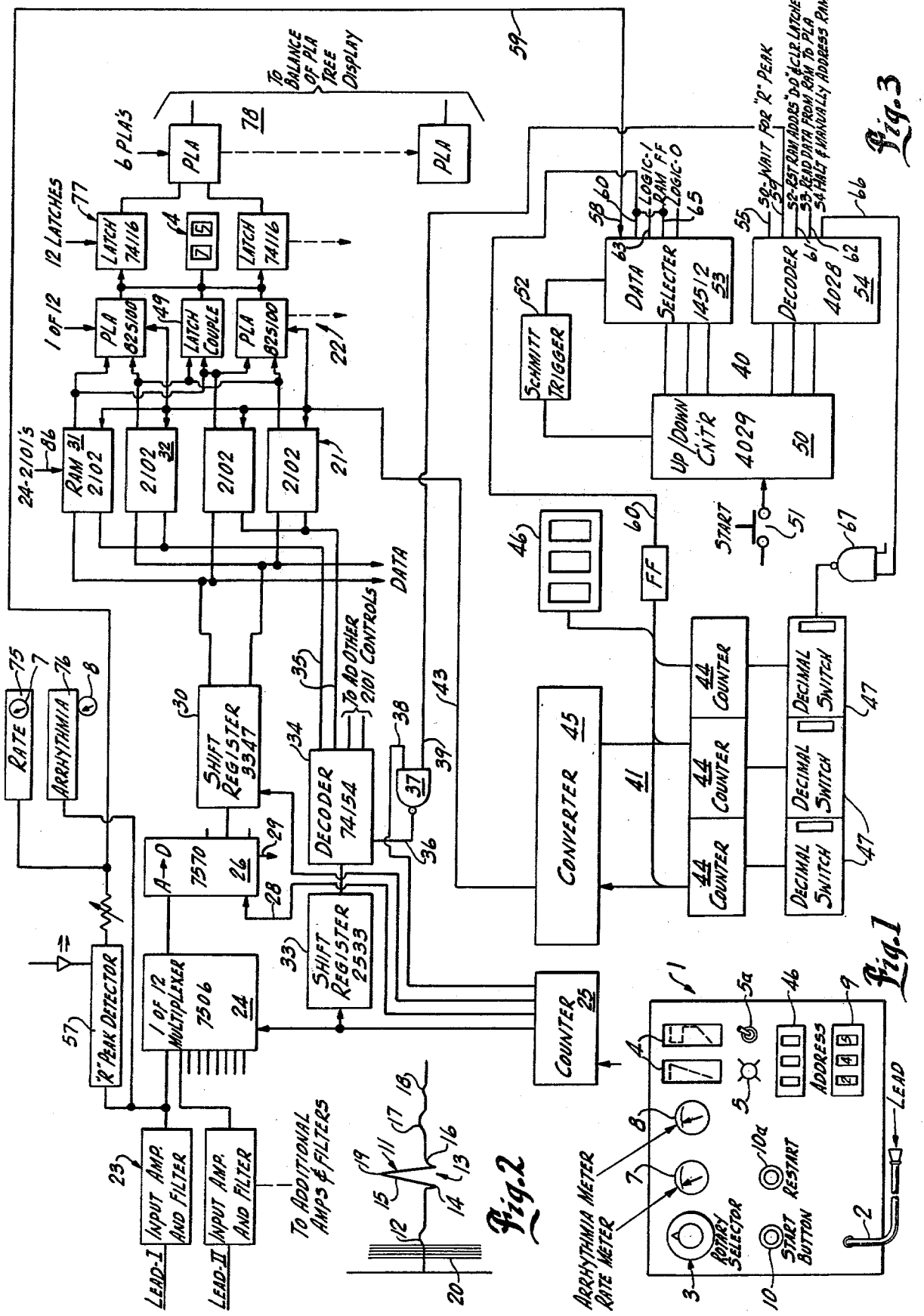

DIAGNOSTIC APPARATUS

BACKGROUND OF THE INVENTION

This invention relates to a diagnostic apparatus for analysis of varying states based on wave shape measurement, and particularly adapted for electrocardiographic and similar graphical analysis.

Electrocardiographic (EKG) analysis, for many years and even today, is based on the recording of EKG waveforms of a patient. Conventionally, a chart recorder includes a plurality of inputs which are adapted to be connected by appropriate leads to various appropriate positions on the patient. The recorder is then operated to record a plurality of different EKG signals. The chart recorder can be operated by suitably trained personnel to produce the series of the EKG charts. A trained cardiologist or specially trained physician can, by study of the EKG waveform charts, analyze the functioning of the patient's heart and determine the presence of any defective conditions.

As a result of past study and analysis, a series of rules applicable to the EKG charts have been developed which permit EKG-trained physicians to properly diagnose the presence of a wide range of heart diseases. The study of EKG charts therefore provides a basis for locating and anticipating abnormal heart conditions as well as subsequent monitoring of the condition of cardiac patients.

Although the chart recorder is a widely employed method of analysis, the requirement of skilled personnel to record the EKG signals and specialized medical personnel to analyze the charts results in a relatively expensive procedure. These features also limit the ready and convenient availability of the procedure.

With the development of computer and digital instruments, computer based diagnostic systems have been developed in which the EKG signals are digitized and stored in memory for computer processing. U.S. Pat. No. 3,698,386 for example suggests use of analog computer and refers to use of a digital computer which requires complex and expensive memory devices. The computer and memory may be on site or, more generally, is remotely located with the EKG signals transmitted over telephone lines or other suitable transmitting means. Analysis of the signals may be provided by various computer programs to produce an analysis similar to the diagnostic logic of the cardiologist. The computer based systems are also generally expensive and of limited availability.

Because of the complexity and costs associated with present devices, they are not therefore adapted to generalized use of clinical mass screening of individuals. As a result, electrocardiographic instruments and analysis are generally available only at hospitals, large medical clinics and the like.

There is, however, a need for a low cost instrument implementing existing clinical knowledge with can be employed without extensive technical training or skill, and therefore adapted for more widespread analysis of heart action and the like.

Many other areas of investigation employ similar analytical techniques in which correlation between recorded varying graphical display provides a basis for investigation of a varying state or condition. Thus, seismographic oil field analysis is based on waveform analysis. Generally, specialized and highly trained personnel are required to obtain the data and more important to analyze the recorded data. Thus, in such fields, improved low cost and reliable diagnostic instruments which can be operated with minimal skill personnel would be desirable.

SUMMARY OF THE PRESENT INVENTION

The present invention is directed to a unique diagnostic instrument in which a waveform is processed and produces a number which uniquely identifies or represents a characteristic of such waveform. The number is related to a standard or reference, with deviation providing a means for detecting abnormal conditions. A standard or reference waveform may be defined by sets of numbers in a logic array, each of which is related to a diagnosis or characteristic in a particular range or portion of the waveform. The instrument converts the signal of a sensing means into numbers which can be directly applied to the reference number logic array and an appropriate signal given in response to an abnormal state. The diagnosis for each may be directly translated by a suitable manual or table. The numeric or diagnostic instrument is simple, reliable and low cost and provides a ready means for direct detection and interpretation of deviation. The invention may particularly provide an electrocardiometer adapted for use in routine physical examinations, mass screening and the field of general medicine.

More particularly, a numeric electrocardiometer instrument includes means for converting the EKG signals associated with the sensing electrode means into a series of unique digital number or word forms. Each number is stored in a suitable memory as a combined time and amplitude number in a dual byte format. A programmed logic array stores a corresponding series of multiple bit time-amplitude byte or numbers defining abnormalities in the EKG waveforms. Each time byte portion of the logic array is generally set with significant and insignificant bits covering a time range or period and each amplitude byte portion is similarly set with significant and insignificant bits covering an amplitude range. Commercially available programmed logic array (PLA) chips may store 48 different numbers. The abnormality numbers define a combination or a class of combinations of a time period of the waveform and an amplitude condition within such waveform period identifying a particular abnormality. The output of the programmed logic array is an identifying code number which identifies the abnormality. Thus, in operation, the waveform numbers are placed in memory. The waveform numbers are read into programmable logic array in synchronism with a time count. The logic array is constructed to make normal-abnormal decisions based on the amplitude of the signal at a particular time count or series of count within a range or portion of a waveform. A binary output number is generated if an abnormality is located and converted to produce the visual code identifying the particular abnormality. Thus, the output may illuminate abnormality indicating lights, may drive a decimal number readout such as a 2-digit LED array or any other suitable output means.

Generally, individual channels may be provided for each EKG lead, indicating its own programmed logic array or a selection means may be provided for sequential connection to a common channel. The output logic functions of the individual channels may, of course, be further combined into a further programmed logic array for overall logic decisions based on the classic twelve leads of a conventional electrocardiogram.

The instrument may also be constructed to display the identifying abnormality digital word or number in the memory. This may be desirable in instruments for use by physicians which can properly interpret the number in the manner of conventional chart recorder. The instrument may further include a printer for printout of the several numbers as well as plotting the output as a series of dots to simulate a chart recorder.

To further assist the analysis, the instruments may also include a heart rate detector and an arrhythmia detector. The rate detector may be a suitable count means for recording the EKG cycles in cycles per minute. The arrhythmia circuit is a suitable circuit which measures the variation in the rate. If the rate exceeds a maximum or minimum rate, an indicator may be operated. Similarly, if an irregular rate and/or other significant abnormality is detected, an appropriate indicator may also be connected to the program logic array particularly in analysis of more complex EKG conditions.

More particularly, in a practical and novel embodiment, a programmed logic array is provided for each EKG lead. An instrumentation amplifier having a common noise rejection means provides an amplified signal which is filtered to remove high frequency noise and applied to the rate and rhythm circuits and to a storage channel. In one embodiment, a multiplexer connects each of a plurality of EKG leads to an analog-to-digital (A/D) converter. In an alternate embodiment, a single lead is provided and the appropriate logic array is enabled. Combinations of these two alternatives may also be used. In each system, the EKG is sampled at a fixed rate and each analog signal is converted by the A/D converter to a digital signal in the form of a digital word or number and written into a time related memory cell or locator in the memory means for the particular lead.

In a highly satisfactory system, the timing is initiated by detecting of the distinct "R" wave peak and the memory addresses are assigned as time segments to the components of the EKG wave. The basic known waveform is then assigned various time segment ranges within which certain significant amplitudes are checked. The several zero crossings of the of the waveform within the time segments may be detected to permit analysis of the various time characteristic of the EKG waveform. A separate logic array may be provided to detect and record each zero crossing, or another array may be employed for detecting each crossing.

A controller is provided for conditioning of the operating system and for sequentially controlling the reading and storing of waveform samples, permitting direct reading of the memory, transfer of the stored numbers to the logic arrays, recording the zero crossings, and the like. The controller in particular includes an analysis state in which a counter is reset and operates to sequentially address the memory and apply such memory numbers in sequence to the individual and corresponding time related program logic arrays. If an abnormal condition arises on a lead within any assigned period of the waveform, the scanning may stop with the corresponding number applied to the program logic array producing an output number. The scan is restarted after appropriate notation of the numbers. An automated fault recording system may, of course, be provided. In the manual restart system, the PLA number may be converted within the instrument to a hexadecimal or decimal number for convenient reading and which identifies the particular abnormality. The operator thus does not need to be versed in the analysis of EKG wave signals, the diagnosis being directly supplied.

Although shown applied as a numeric electrocardiometer, the invention is applicable to any application in which data or information is available as an electrical signal in which the shape of a related waveform contains the information, which can be related to empirically or analytically generated numbers stored in a logic array. The present invention thus may provide a simple, reliable and inexpensive instrument for analysis of waveform deviations without the necessity of specialized knowledge of the waveform characteristics as such.

BRIEF DESCRIPTION OF DRAWINGS

The drawings furnished herewith illustrate a preferred construction and best embodiment of the present invention as presently contemplated by the inventor in which the above advantages and features are clearly disclosed as well as others which will be readily understood from the following description.

In the drawings:

FIG. 1 is a diagrammatic illustration of an EKG electrocardiometer instrument constructed in accordance with the teaching of the present invention;

FIG. 2 is a simplified illustration of an EKG waveform;

FIG. 3 is a block diagram illustration of an electrocardiometer shown in FIG. 1;

DESCRIPTION OF ILLUSTRATED EMBODIMENT

Figure 3A:
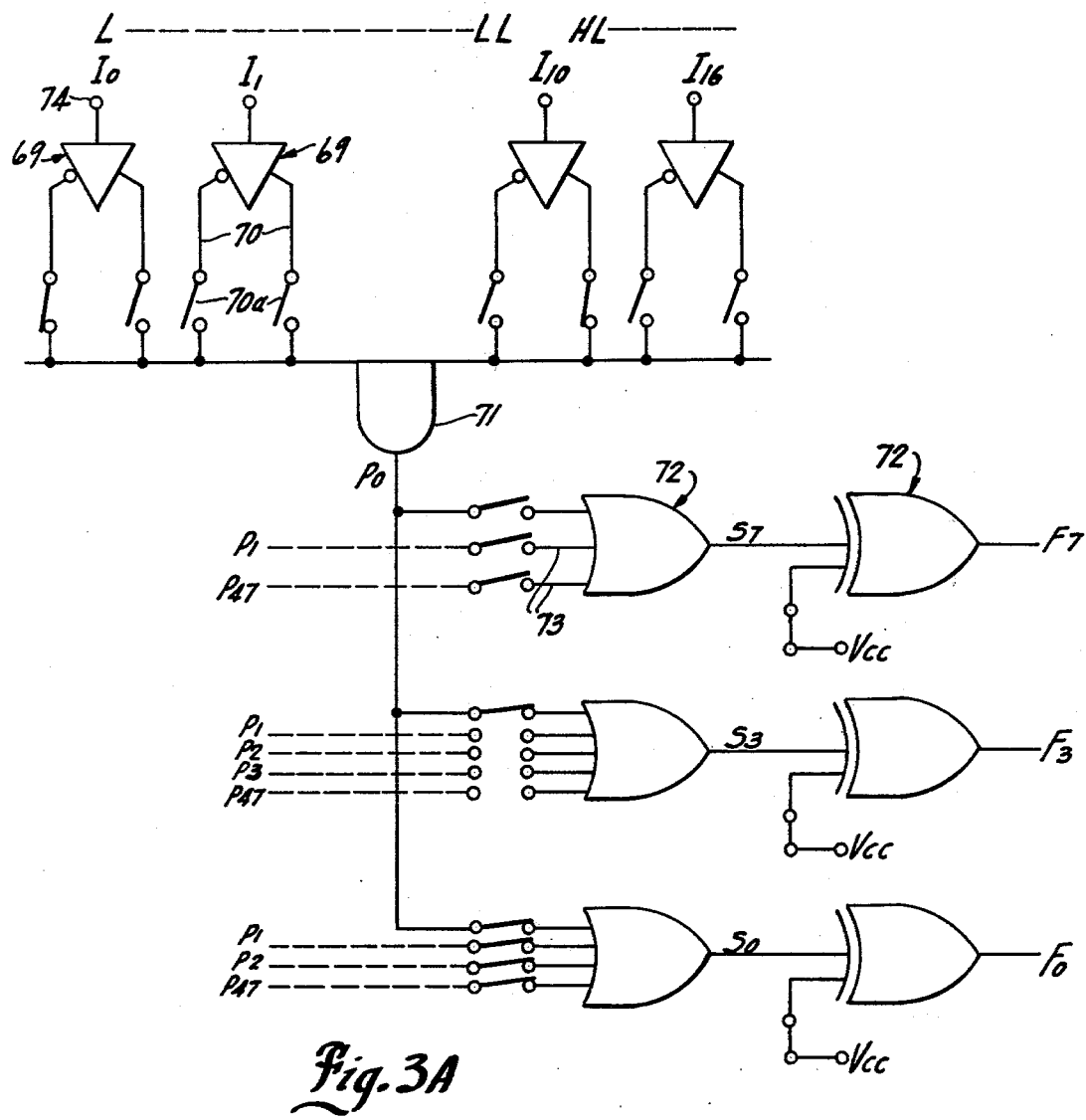
FIG. 3a is an illustration of a programmed logic array showing a part of the internal logic circuitry.

Referring to the drawings and particularly to FIG. 1, the electrocardiometer instrument 1 is illustrated including a plurality of EKG leads 2 for interconnection of the instrument to the appropriate portions of the human body, not shown. Generally, in accordance with conventional practice, twelve separate individual EKG leads 2 may be provided or three leads 2 may be provided monitoring of the body functions, each of which is adapted to provide an appropriate waveform signal relating to the functioning of the heart. Alternatively, a single lead 2 may be provided with an EKG lead selecting control 3 provided for selecting of the function.

In accordance with the present invention, the waveform signals are stored in a series of identifying time and amplitude or sample numbers which are related to corresponding numbers providing numeric indications of a cardiac condition or waveform based on predetermined and known combinations of time and data samples, and in response to a selected deviation an output signal is generated and selectively displayed as an identifying number on a display unit 4. In the illustrated embodiment of the invention, a hexadecimal number display unit 4 provides a two digit display. The identifying number directly identifies particular heart conditions, and particularly abnormal conditions.

Generally, the personnel operating the instrument need not, of course, directly memorize the related heart conditions associated with each identifying number. The information can be readily provided directly through an appropriate manual or through a suitable conversion device, if desired, and which could include a suitable printout device or the like.

An alarm lamp 5 is shown to provide a visual signal whenever an abnormal heart condition is detected. The lit lamp 5 attracts the operators attention at which time he can readily read the digital number display unit 4, thereby determining the particular heart condition detected. In addition and as more fully developed hereinafter, the instrument 1 preferably includes means to detect appropriate rate and rhythm conditions of the heart. Meters 7 and 8 are provided to indicate such a failure or alarm condition to the operator. In addition, each stored number may be directly read by an address input shown as a 3 digit control 9.

A start button 10 is provided for initiating operation of the instrument. The instrument is then conditioned to start for sequential analysis of the waveform data provided at any given lead. If an abnormality is located the instrument stops scanning and holds the identifying number in display unit 4. A restart button 10a is provided to reinitiate the cycle from the last read portion.

More particularly, a simplified EKG waveform 11 is illustrated in FIG. 2. The waveform 11 includes an initial P wave 12 connected by a dwell period to the Q-R-S wave 13. The latter includes a relatively small negative Q wave 14 connected to large positive spike or R wave 15 and a small negative spike or S wave 16. The waveform is completed by a T wave 17 shortly following the S wave 16 and may include a small final U wave 18 as illustrated. As shown in the amplitude of the R wave 15 is much greater than any of the other position of the waveform 11. In accordance with the present invention, as hereinafter described, the R wave peak 19 which is always a sharp spike with rapid change in slope is employed as a convenient reference or key from which the recording of the waveform is initiated. The total waveform is divided into a plurality of equally spaced sampling segments, shown diagrammatically by sampling time, lines 20. In one system, each complete wave starting with peak 19 included 256 equally spaced samples, providing a suitable number of samples for proper analysis of the characteristic of the EKG waveform. A typical or standard waveform is stored as a series of 256 samples as an amplitude-time signal for each sample.

The sampled waveform data is read into the instrument 1 compared with the standard EKG waveform data for that particular lead and any abnormal or predesigned deviations related to a particular abnormality is converted to an identifying number which in turn is displayed on the number display unit 4. Generally, as shown in FIG. 3, each waveform is continuously sampled and each such segment sample placed into an appropriate memory or unit 21. After sampling of a complete waveform, the waveform data samples are fed to a programmed logic array 22 which has been programmed with normal amplitude-time digital data, such that each reference input monitors the state of any one data sample or series of data samples as the data is swept into the logic array. The data or any given sample is directly compared with a single reference or a range by each logic array 22 which is programmed to produce a given number of outputs. Any abnormality is detected and converted into the appropriate encoded number and displayed on the readout 4. Each segment 20 has a particularly and unique memory and array address. In addition, any particular identifying segment 20 of the waveform can be recalled by the operating personnel at will through the use of number selection or address means 9 which directly addresses the memory unit 21 and transfers the stored data number to readout 4, either in binary form, or with appropriate readout means in conventional decimal number, identifying the amplitude of the time segment. If the operating person has the particular skill of a trained cardiographic physician, he can then directly analyze and check the heart characteristics to determine the actual heart waveform and the particular abnormality.

This provides a very simple instrument adapted for mass screening of individuals and is particularly adapted to use by physicians who specialize in the general practice of medicine in contrast to the specialized practice.

A particularly satisfactory embodiment of the invention is shown in block diagram in FIG. 3 in which the several elements for successively sampling and storing of the waveforms of a plurality of leads 2, comparison of the each waveform and readout relating thereto are illustrated.

More particularly, in FIG. 3, each of a plurality of leads 2 is connected to an input amplifier and filter units 23. The output of the several units 23 are connected to an individual and assigned input of a standard multiplexing unit 24 having a common or single output. A counter 25 operates to continuously cycle the multiplexing unit 24 in timed spaced sequence for sequentially and repetitive sampling and transfer of the waveforms to the processing channels. The counter 25 is operated from a suitable clock unit not shown, maintaining synchronous operation of the several components of the system. The output of the multiplexer 24 is applied to a suitable digital-to-analog converter 26 for converting of the analog signal into a related digital sample or signal suitable for storage in digital memory unit 21. The A/D converter 26 includes a start clock input 28 connected to the time clock and a busy output 29. The digital output representation is transmitted to a shift register 30 which is operated in response to the busy signal output of the A/D converter 26. The output of shift register 30 is coupled to the RAM memory unit 21. A pair of RAM memory chips 31 and 32 may be provided for each lead. Each amplitude signal is stored as an 8 bit word with the most significant bit identifying and distinguishing positive and negative amplitudes. For convenience of construction each of the 8 bit words is divided into a pair of 4 bit words stored in the respective related memories 31 and 32, such that a relatively inexpensive RAM memory assembly can be employed. Thus, in the illustrated embodiment of the invention, with twelve leads 2 provided, 24 RAM memory chips would be provided. As previously noted, 256 samples are to be stored in each memory unit and the illustrated memory units have the capacity of storing a total of 256 bytes, each of which correlate the time and sample data in dual byte format.

The waveform samples are placed in particular memory cells or locations having unique addresses. In FIG.

3, a memory read input is generated in timed relation to the waveform sampling and the transfer of the data. A shift register 33 has a clock input connected to counter 25. The output of the shift register 33 is thus operated in synchronism with the multiplexing unit 24 and the A/D converter 26 and provides an appropriate output signal to a decoder 34. The decoder 34 includes a pair of output lines 35 connected one each to the appropriate memory write inputs of the memory pairs 31 and 32. The decoder 34 in turn includes an enable input 36 which is connected by a NAND gate 37 having one input 38 connected to the clock and a second loading input 39 connected to a state controller 40. The state controller 40 provides continuous monitoring of the state of the instrument and provides appropriate sequential operation signals to the several components of the unit including a load signal at line 39. The decoder 34 introduces a delay into the transfer, and the addressing of the memory unit locations is coincident with the inputting of data from the shift register 30 into memory 21. The addressing is provided by an address counter unit 41 operated in synchronism with the multiplexer 24 and the A/D converter 26.

The output of counter unit 41 is connected to the RAM memory units 21 and to the logic array chips 22 via an 8 bit wide address bus 43. Counter unit 41 is shown including a counter 44 for each significant decimal position and connection to decimal to binary number converter 45 connected to bus 43.

After placing of the waveform data samples in memory, the controller 40 reads the dual time and sample data bytes into the logic array 22 for instantaneous detection of the correlated time and data sample bytes for providing numeric indication of waveform normality and abnormality based on each combined time-sample data byte, and finally establishes a halt period during which the operator can selectively readout any address in memory by setting of the address controls 9, with a visual display on a suitable display unit 46 shown as a conventional three digit decimal readout. Each control 9 activates an encoding switch 47, the output of which is applied to the corresponding counter 44 to actuate counter unit 41 to establish the corresponding address on bus 43. Thus, the memory unit 21 has the data output lines or buses connected to coupling unit 49 for direct connection to the readout unit 4.

The illustrated state controller 40 includes a counter 50 having a start control input switch 51 coupled to the input button to recycle the counter. The counter is driven from a gated oscillator 52 such as a Schmitt Trigger which is triggered from an instrument function and data detector 53 to provide sequential time spaced control signals. The output of the counter 50 is connected to drive the selector 53 and a state decoder 54 for actuating the instrument components. The output of the state decoder 54 establishes a plurality of five state control signals at corresponding state lines which are connected to the system components for purposes of sequentially activating the several components. The selector 53 detects certain conditions and completion of internal processes within the waveform recording and comparison event and provides a signal for sequencing the change of state.

For example, as previously noted the illustrated embodiment of the present invention preferably initiates a sampling from the peak 19 of the "R" wave 15 of the EKG waveform 11. When the system starts, the decoder 54 establishes a "wait for" peak signal at a related output line 55. The signal is applied to the system to establish a free running state such that data is continuously brought into the A/D converter 26. An "R" peak detector 57 is connected to lead 2 and produces an output signal at and only at the peak. The detector 57 is connected to an "R" peak input 58 of selector 53.

When the "R" wave peak 19 is detected, the input 58 results in operation of the counter 50 to drive the decoder 54 to the second state. A second state line 59 is connected to decode 34 to load the waveform data from the register 30 into the addressed memory location. The second state maintains the reading and loading of data to memory 21 to the final location, or number 256 address. The address generator 41 then generates an "F-F" or number 256 signal, which is connected to an input line 60 of selector 53. The decoder 54 then steps to state 3 and generates a signal at line 61 to clear the addresses and then at a line 62 to transfer and read the data from memory 21 to the programmed logic array 22.

The selector 53 has a logical line 63 which steps automatically to produce a timed period during which the address generator resets. The selector 53 then again steps the counter 50 and the decoder 54 moves to state five, with a state line 62 which signals the systems to read data from the RAM memory to the logic array unit 22. The selector 53 is then set to again respond to generation of address "F-F" at line 65, and again step the selector and decoder, which enters a stop or halt state and activates a line 66. The signal at line 66 enables the input address switches 47 for manually addressing of memory 21 for review of the state of the waveform.

Thus, the address generator 41 includes a dual input NAND gate 67 having a pair of inverting inputs connected respectively to a third clock output and to the state four line 66 of the decoder. Thus, both of these conditions must exist at which time it is appropriate to transfer the RAM data.

The programmed logic array assembly 22 includes a plurality of individual chips, each of which may store a plurality of conditions or time-sample data bytes and by comparison with the actual waveform produce a product term or number which uniquely identifies any abnormality or programmed deviation of the waveform in memory 21.

FIG. 3a is a simplified schematic of a typical programmed logic array chip manufactured and sold by Signitics and which are field programmable. The input to the chip includes 16 inputs I through I. Each input is connected by a logic gate 69 to a pair of fused or switched logic lines 70 having switches 70a. The lines 70 are connected by an AND gate 71 to a summing matrix or "OR" gate 72. Each "OR" gate has a plurality of inputs 73, one for each set of inputs 74. Thus, the input terminals are parallel hardwired or connected to the input signals from the memory and the read gates enabled to read the appropriate condition. The chip is programmed by closing of the switch lines 70, as by turning and once programmed defines the point and more significantly may define a range or portion of the waveform. As shown in FIG. 3a, input $I_0$, $I_8$, $I_9$, and $I_{11}$, have the inverted output closed producing a low signal, and line $I_{10}$ has a non-inverted output line closed producing a high signal. All others are both open and the input can be high or low without changing the product term; the latter inputs are therefore not significant to the final product term. This is highly significant in the present invention because it permits each statement to define a time and shape range of the waveform and the related information. The output or product term results in an eight-bit product in which $F_0$ and $F_3$ are high. If the input waveform sample stored in memory and the time signal which are read into this chip array meets the conditions set by the switches 70 the output is a hexadecimal number, which is displayed in readout 4.

The addressing of the logic array produces a time signal input based on the timed sampling of the waveform. Thus, the addresses $I_0$ through $I_7$ are connected to the address counter 41 and identify the time slot.

The addresses $I_8$ through $I_{15}$ are connected to memory 21, at the appropriate address, and supply the amplitude number. The chip is thus programmed to respond to certain amplitude conditions at or during certain time periods.

Thus, as previously discussed, the waveform is separated into assigned time periods during which basic waveshapes occur. The program logic chip is then programmed to scan the total 256 memory locations, but only responds to numbers which appear in particular time slots. For example, the total time sample will be greater than the time of the varying EKG waveform 11, such as shown in FIG. 2, but less than the time to overlap between waveforms. Ths time is then assigned to the waveform with the "R" peaks 19 at a known time; for example, time 80 in which the chip is programmed for the following conditions:

| ADDRESS (TIME) | WAVE COMPONENT |
|---|---|
| 0–44 | No signal |
| 45–65 | P-Wave (12) (usually positive) |
| 66–72 | P-Q Segment (usually zero) |
| 73–78 | Q-Wave (14) (values are negative) |
| 77–83 | R-Wave (15) (values are positive) |
| 83–87 | S-Wave (16) (values are negative) |
| 86–104 | S-T Segment (usually zero, but sometimes ± 0.1 mv) |
| 103–121 | T-Wave (17) (usually positive) |
| 121–256 | U-Wave (18) or no signal |

Within each time segment, the amplitude signal should be of a particular value or ranges. In the illustrated embodiment, the significant waveform is stored within the first half of the memory.

Each chip can store up to 48 different product terms or statements for a time and amplitude sample data and thus conditions normality and abnormality of the waveforms. A lead 2 may be programmed to detect the appropriate significant portions of such waveform. Thus, for a conventional EKG lead II, the implementation or programming may be as follows where L=Low or logic "0" and H=high or logic "1". The dashes in the number or words indicate that the programming may be either high or low and thus constitutes a "don't care" input such that a range or portion of the waveform may be covered in each statement or time and sample data byte:

| No. | Criteria | Implementation | |
|---|---|---|---|
| 0. | P=0.3mv | T=LLHL---- | $32 \leq + \leq 47$ |
|    |          | A=H---HHHH | A <300 NV |
| 1. | −P | T=LLHL---- | $32 \leq + \leq 47$ |
|    |    | A=L------- | A <−20 NV |
| 2. | Q=−0.25 mv | T=LHLLHL-- | $72 \leq + \leq 75$ |
|    |            | A=L---LL-- | A <−240 NV $\leq 300$ NV |
| 3. | Q=0.25 mv | T=LHLLHL-- | $72 \leq + \leq 75$ |
|    |           | A L--L--- | A $\leq −320$ NV |

-continued

| No. | Criteria | Implementation | |
|---|---|---|---|
| 4. | R=0.15 mv | T=LHLHLLLL | =80 |
|    |           | A=HLLLL--- | A <160 NV |
| 5. | (S-T(=−0.9 mv | T=LHLHH--- | $88 \leq \pm \leq 95$ |
|    |               | A=L-LL---- | A $\leq −960$ |
| 6. | (S-T=) 0.9 mv | T=LHLHH--- | $88 \leq + \leq 95$ |
|    |               | A=HLHH---- | A 960 |
| 7. | −T= | T=LHH-H--- | $104 \leq \pm \leq 127$ |
|    |     | A=L------- | A $\leq −20$ NV |
| 8. | T=1 mv | T=LHH-H--- | $104 \leq + \leq 127$ |
|    |        | A=HL------ | A $\leq 1280$ |

The amplitude is of course scaled employing appropriate 8 bit binary numbers. Although a 256 word memory is employed, only a portion is employed to record actual data to provide a housekeeping period between successive sweeps. Thus in the above example, only 128 time segments span the useful data, with the other time segments being effectively zero data sampled. The output of the PLA units 22 which are conventionally in Hexadecimal format may be converted to the more usual decimal readout in display 4. The most significant bit in the amplitude number distinguishes positive and negative numbers.

As previously noted, the instrument preferably provides means for detection of the heart rate and arrhythmia. The output of the "R" peak detector 57 is shown connected to a heart rate recorder 75 which detects the successive peaks and produces a reading on the meter 7. An arrhythmia detector 76 is connected to input waveform signal and produces a related readout on meter 8.

When running a waveform sequence, the operator can readily determine the basic heart condition to determine whether the fuller analysis provided by the instrument would be useful. The waveform is read from memory as a series of 0 to 256 time segment samples of the waveform into the PLA unit 22. Simultaneously the timer segment word or address is applied to the PLA unit 22. If the time and amplitude signals match the implementation, the output of the PLA unit 22 goes high and drives display unit 4

An error readout may terminate further processing and allow the operator to record the number as presented on display unit 44 and take any desired action. An automatic printer or other storage device could of course be employed to automatically capture and record each fault signal and address number. When the instrument halts processing, the manual restart means 10a is actuated to continue sequencing, as more fully discussed hereinafter.

Further, as shown in FIG. 3, the PLA outputs may be placed in suitable latches 77 and the combined outputs applied to set of PLA units 78 arranged in a tree display as noted for analysis of the various combination and permutations provided by the characteristics of the individual leads.

Although any suitable signal processing and logic circuits can be employed, a preferred construction is shown in FIGS. 4 through 7. Thus, the several components illustrated in FIG. 3 are readily available and known components and the construction of embodiment can be readily completed as shown. In the embodiment of FIGS. 4–7, a preferred embodiment is structured for employing a single lead 2, with the selection control 3 provided for enabling a programmed logic chip or unit 22 assigned in accordance with the EKG lead identification. The common components such as the memory and PLA units are corresponding numbers, for purposes of simplicity and clarity of explanation.

Figure 4:
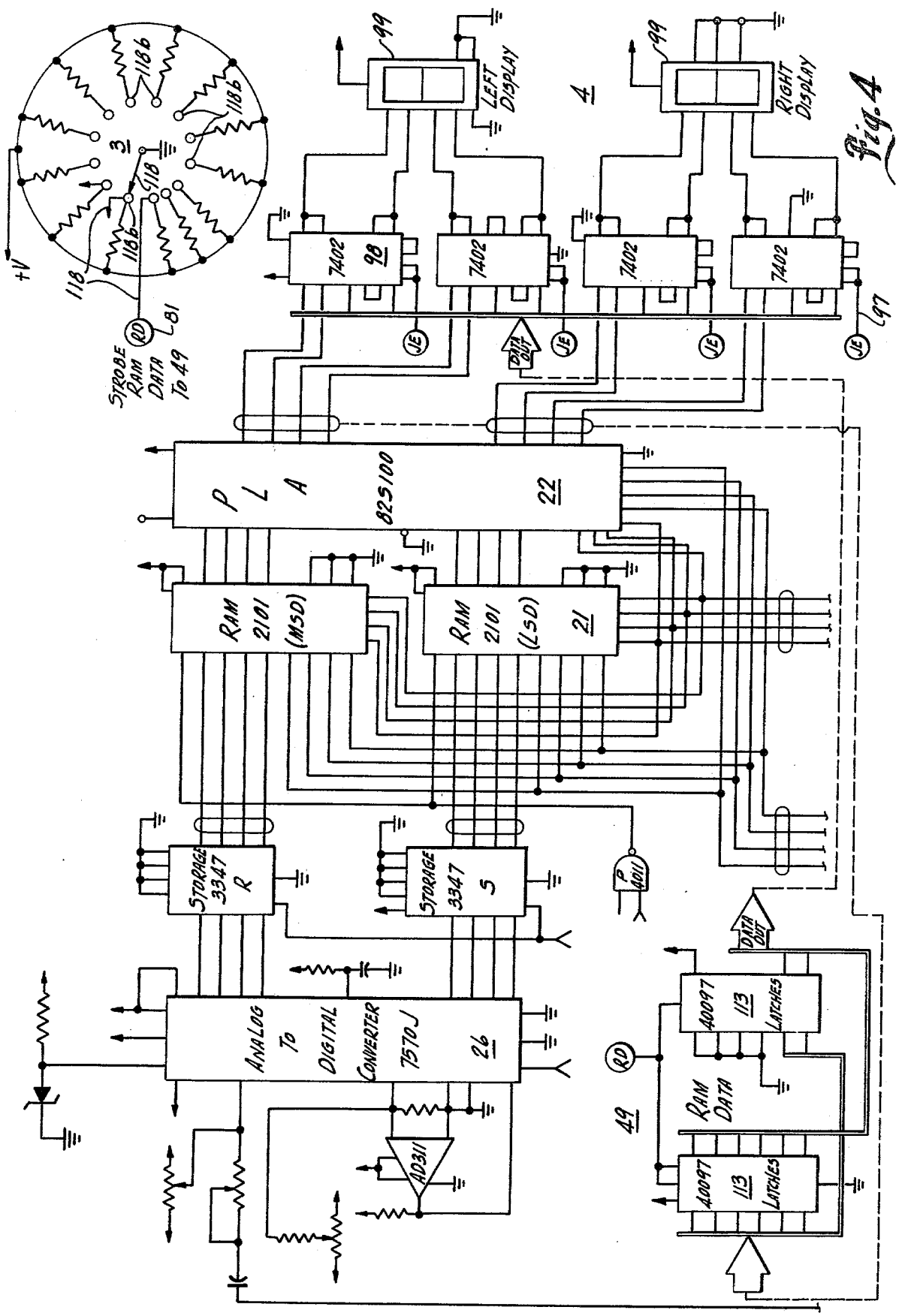
FIG. 4 is an expanded view of the memory and logic array shown in block diagram in FIG. 3 and further illustrating construction of the instrument with essentially readily available circuit components.
Figure 5:
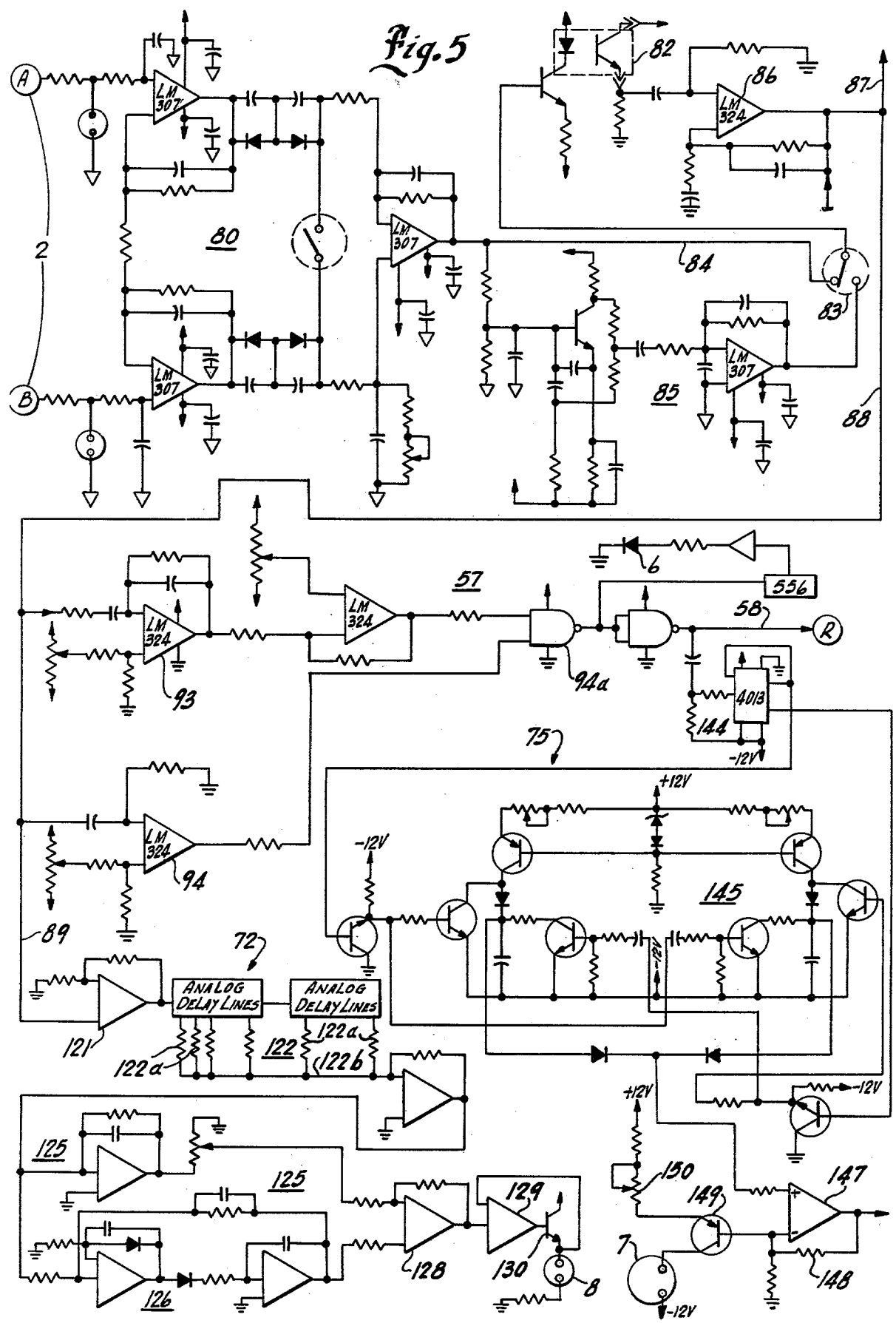
FIG. 5 is a view of the signal input processing circuit of FIG. 3.

Referring particularly to FIG. 5, the multiplexer 24 of FIG. 3 is not employed and the A/D converter 26 is connected to a single lead 2 via a coupling circuit more fully disclosed in FIG. 4. The converter 26 again samples and digitizes the waveform signal at a sample rate set by the clock unit, a suitable construction herein shown in FIG. 7.

The input analog waveforms signal is processed and applied to the amplifier and to the "R" peak detector 57 in a suitable circuit such as shown in FIG. 5. The illustrated circuit includes an operational amplifier 80 connected as a standard differential instrumentation amplifier. The output line 81 of the amplifier is connected to a signal isolating circuit 82 by a selection switch 83, coupled to control 5a. The signal is coupled directly in one switch position via a lead 84, to circuit 82 and through a narrow b and, low pass filter 85 in the alternate switch position. The filter is employed to filter out unwanted high frequency and particularly 60 cycle signals. The processed analog signal is connected by an input amplifier 86 to the input of the A/D converter 26 of FIG. 5 via lead 87 and to the R-peak detector circuit 57 via a lead 88 and via a lead 89 to the arrhythmia unit 72.

In FIG. 4, detector circuit 57 is shown including a pair of inputs, one to a differentiating amplifier 93 and the other a threshold amplifier 94. A two-input NAND gate circuit 94a is connected to amplifier 93 and 94 and to produce a signal at the "R" peak 19, and only if such peak is relatively sharp and well defined peak. The output is also connected to a lamp 6 shown as an LED unit, which indicates the circuit is in operation.

The output of detector 57 is of course applied to the input line 58 of the controller 40, which initiates the previously described cycle of transfer of the digitized signals to RAM memory from the storage registers 30. The processing circuit of FIG. 4 is described, with the rate and arrythmia circuits shown in FIG. 5 hereinafter described. The detail of a control 40 and address counter 41 are shown in FIG. 6, for the processing circuit of FIG. 4.

Figure 6:
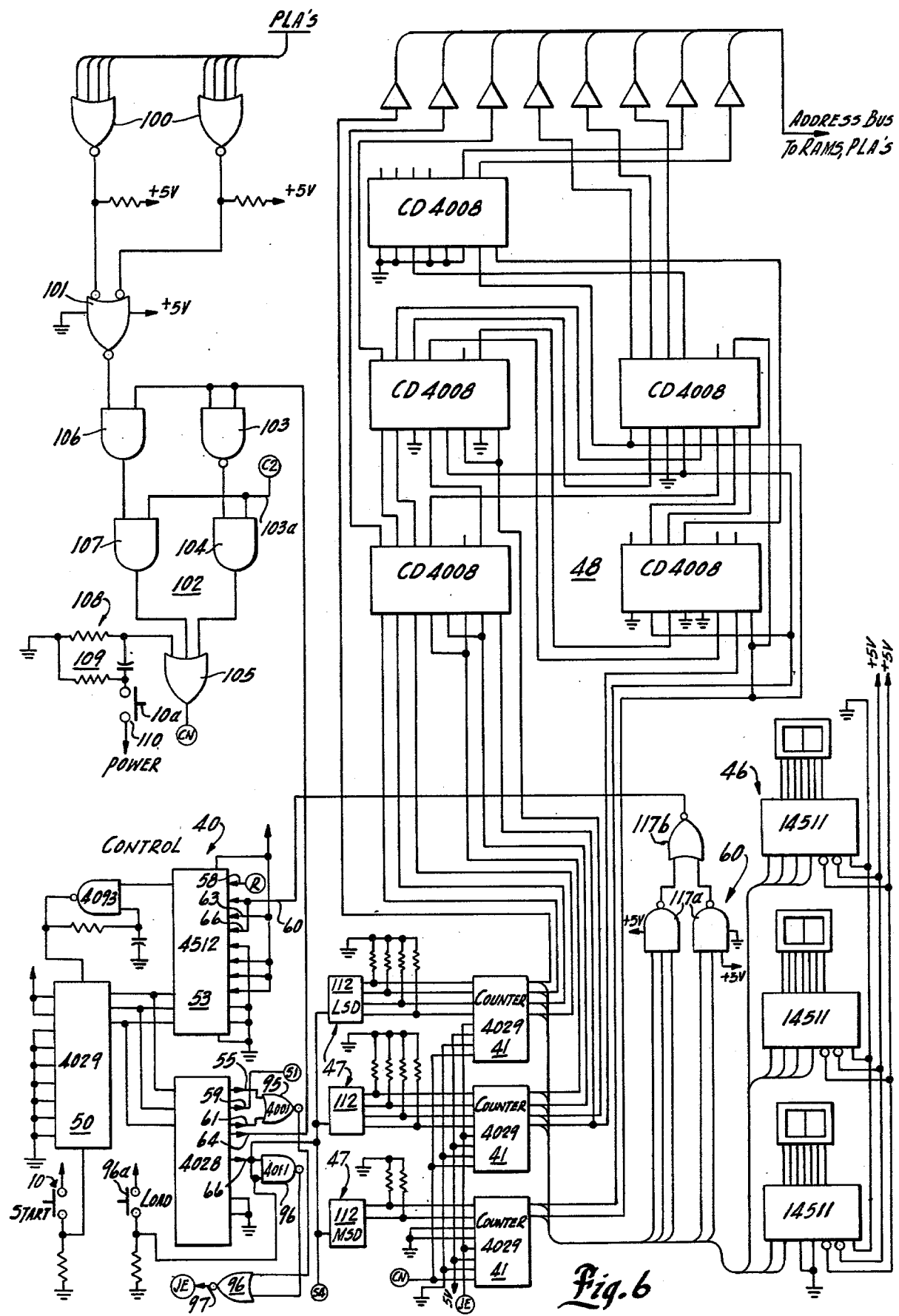
FIG. 6 is a view of the memory and logic array addressing means and of the controller, shown in block diagram in FIG. 3.

Thus, as shown, in FIG. 6, the controller in state "0", 2 and 4 operate to reset the counter and clear the latches. Thus, state "0" and 2 lines 55 and 61 are connected to a first NOR gate 95 and its output and state "4" lines 64 connected to a second NOR gate 96. The state "4" line is ended with a manual load signal line including a load switch 96a for manually halting operations for addressing memory 21. The output of the second NOR gate 96 produces a jam enable signal at a line 97, which is connected to the counter 41 as shown in FIG. 6 and to the readout circuit for the logic array units 22, as shown in FIG. 4.

The output of the each programmed logic units 22 is parallel connected to a set of register units 98, each of which includes an enable input connected to line 97. A pair of units 98 are provided for reading each of the most significant and least significant bits of the hexadecimal number output of the enabled logic array unit 22. The output of the registers 98 are connected to a suitable display elements 99 forming the display unit 4. The readout and conversion forms a standard system for conversion of binary numbers to a conventional decimal readout rather than the hexidecimal readout or the like such as encountered in computer and similar technology.

The one logic array unit 22 is programmed to detect each zero crossing of the waveform and readout the time segment 20. A separate array unit 22 may be provided, on the unit for the usual AVR lead may be employed. Thus, the zero crossing PLA would be continuously enabled. The zero unit 22 is programmed as to time and amplitude to indicate the equivalent of an abnormal condition whenever a zero-amplitude segment stored in the RAM memory unit 21 is detected within a time segment assigned to the various pulse signals of the waveform 11. The reading sequence is terminated at this point to permit recording of the time segment, either manually by the operator or automatically as by attachment of suitable printer/coupled to the readout.

Each time the sequence scan is thus stopped, the address of course is displayed in the address readout unit 46 and the operator can directly read the address for such conditions.

A suitable stop circuit is shown in FIG. 6, wherein the output of each time logic array unit 22 including the special time logic array unit 22, if used, is coupled to a pair of NOR gates 100 each of which produces a high logic output whenever the output goes high, such as when a zero crossing is detected. The output is gated to a two input NOR gate 101, the output of which is combined in a clock signal control network 102, with a scan control signal related to state 3 from the state controller 40. The network 102 includes a normal clock transmission channel and a second stop clock transmission channel. The first channel of network 102 includes a first NAND gate 103 having both inputs connected to the state 3 control signal line 64. An AND gate 104 has inputs connected to the NAND gate 103 and the second input connected to the number 2 clock signal line 76 FIG. 6. Thus, in all but state 3, the clock signal, is transmitted via AND gate 104; and is connected via a NOR gate 105 to the address counter 41. As state 3, gate 103 produces a low output and effectively opens gate 104. The second channel, connected to the stop signal gate 101, includes an AND gate 106 which combines the zero signal from gate 101 with the state signal line 64. The output is coupled to the clock signal in an AND gate 107. Gate 107 produces an output clock pulse unless gate 101 introduces a low signal, signaling a fault condition. The output of gate 107 is connected to NOR gate 105 for generating of an address clock signal. The NOR 105 thus produces a clock signal in all states under normal waveform conditions, with state 3 being specially monitored to stop the operation of the counter at any abnormality including a zero crossing. A restart circuit 108, shown a simple pulse forming means 109 connected to power by a switch 110 generates a pulse signal in response to actuation of a restart switch 110. The latter is coupled to the push button restart button 10a. The pulse is connected via the gating network to actuate the counter 41 to advance one address and thereby again start the sequence of loading the data from memory into the enabled PLA logic unit 22. The loading continues until the next zero crossing or other abnormality, at which time the above stop sequence is again created.

As previously noted, the digital number stored in any memory cell or location may also be read out directly.

The memory is addressed by the three decimal number input 9, which as shown in FIG. 6, are suitable switch units 112 for producing a decimal number output. The switches are connected to the state 4 "halt"

line 66 of the decoder 54 thus only enabled during this state of the controller. The switch units 112 are coupled to the three counters 41, the outputs of which are connected to an appropriate and standard decimal to binary converter circuit 48 which converts the decimal number to an appropriate binary number at the address bus 45 to the ram memories 21 and the logic array units 22. The jam enable signal is created in this state 4, as a result of the connection of the gate 96 to the state 4 "halt" line 65 via the NAND gate 96a. The counter 41 thus establishes the selected address for readout of the binary number stored in that location which is readout through unit 49. The selector 3 includes a readout position which grounds the enable contact 81 connected to the enable input of unit 49. The unit 49 (FIG. 4) includes a pair of latch units 113 having the inputs wired to the data outputs of the total memory 21. The output of the latches is connected to the registers 98 and the stored data is readout as a decimal number on readout 4. The selected address is also readout an address display unit 46 as shown in FIG. 6. Thus, the outputs of the counters 44 are coupled to lamp display drivers 114 for driving a 7 segment display. The display 46 is also driven during the automated sequencing and of course provides a readout whenever the unit is stopped by a fault condition.

This permits further detailed analysis of the waveform data.

Figure 7:
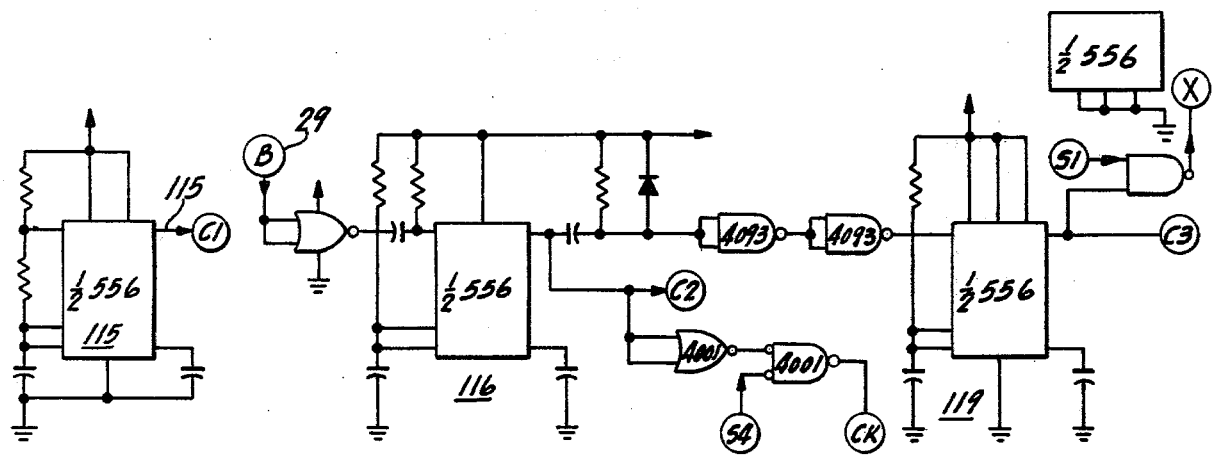
FIG. 7 is a schematic circuit of a clock means for the circuits of FIGS. 2 through 6.

In FIG. 7, the clock unit 25 includes a first clock 115 of known design producing a continuous series of time spaced signals at a C1 output line 115 a which is connected to the clock input 28 of the converter 26. A triggered clock 116 has an input connected by an inverting type gate to the busy or done output line 29 of the A/D converter 26 and is operative to produce a time delay second clock signal connected to the shift register 30 and to the address counter 41 via the clock circuit 102 and input line 103a.

This as previously described enables and starts the address counters 41, which initiate the addressing of memory bank 21 for loading of the digital memory cell location with the digitized samples (FIG. 4) and/or the PLA's for reading of the memory. The memory cell locations are of course sequentially addressed and the addresses are thus related to the time segments lines 20. The counters 44 of unit 41 have their appropriate outputs connected to the logic unit 60 including the pair of NAND gates 117a and a NOR gate 117b such that gate goes high at the number 256 or hexadecimal number "FF". Gate 117b is connected to the line 60 of the state controller 40 and produces a signal that all 256 segments have been placed in storage, and that the data can be loaded into memory and thereafter into the logic array 22. (FIG. 6)

As noted, FIGS. 4 through 7 provide for use of a single lead 2 with selection of the appropriate array 22 by rotary control 3. As shown in FIG. 4, the rotary control 3 is a rotary switch unit having a ground rotary contact 118 selectively engaging one of a plurality of contacts 118b, which are each connected to enable input 118c of a different logic array unit 22 and to a direct memory read unit 49, as shown by the connecting lead. Contacts 118b normally are high and only that connected to rotary contact 118 is low to enable the corresponding chip. Thus, the data stored in memory units 31 and 32 can be transferred to the appropriate enabled logic array unit 22.

The clock unit 25, as shown in FIG. 7, has a third triggered clock 119 having its trigger input connected to the output of the second clock 116. The output of clock 119 is connected to the two input NAND gate 37, shown above in FIG. 3. The second input of gate 37 is connected to state controller 40 and particularly the RAM load line 59. The output 36 of the gate 37 is connected to actuate the read input of the memory chips 31 and 32.

In summary, the operator selects the desired logic array unit 22 by setting of the rotary switch 3. The lead 2 is attached and the start button actuated. The waveform data is digitized by the A/D converter 26. The controller 40 waits for the signal from the "R" peak detector 57 to step to the state for loading the RAM memory 21, and to then impress the memory to the logic array unit 22 and permit the previous analysis. If, however, an abnormal rate characteristic is detected, the arrthymia circuit 72 may actuate meter 8 and signals to the operating personnel the more severe problem which makes the normal analysis generally non-productive.

The arrthymia circuit 72 is constructed to detect sufficiently distorted heart rate rhythm in which normal analysis is non-productive. The monitoring personnel is thus directly and immediately informed of the severe or unique problem presented. The illustrated arrthymia circuit an input amplifier 121 connected to the output of the opto-isolating unit 82 to directly receive the waveform signal. A matched filter 122 having a plurality of preset stages each includes a level setting resistor 122a shown as sixty-four resistors connected to a common output line 122b. The amplified heart wave signal is impressed on the filter 122 and particularly is clocked into the filter as 64 samples for each complete sample cycle. The several outputs are summated on the output signal line 122b and applied to an amplifier 123, the output of which is connected to a rate cycle detection circuit 125. The value of the resistor 122a sets the particular waveshape which will produce a maximum output. A waveshape which deviates from such preset pattern or waveshape results in a reduced output.

The detection circuit 125 includes an averaging or smoothing branch 126 and a peak detector branch 127 connected directly to the output of the amplifier 123. A difference amplifier 128 generates an output signal in accordance with the difference between the average signal and the peak signal. The difference signal effectively removes the effect of extraneous, momentary signals and produces a more reliable arrthymia signal.

The signal is applied to a switching amplifier 129, the output of which drives a driver transistor 130 connected in series with an output indicating unit shown as the suitable meter 8.

The averaging or smoothing branch 126 includes an operational amplifier 131 having a non-inverting input connected to the amplifier 123. A feedback network 132 including a paralleled capacitor and resistor connects the amplifier output to the input. A potentiometer 134 in series with a fixed resistor 135 connects the average output to the non-inverting input of the difference amplifier 128.

The peak detector branch 127 similarly includes an operational amplifier 136 having its inverting input connected to the match filter amplifier 123. The inverting input connected to ground. A feedback network 137 includes a capacitor in parallel with a diode connecting the inverting input to the amplifier output. A diode 138 in series with a resistor 139 connects the amplifier 136 to the non-inverting input of a second operational amplifier 140, having a feedback coupling capacitor 141. A feedback branch from amplifier 140 to the inverting input of the amplifier 136 includes a paralleled capacitor and resistor network 143 such that the amplifier 140 provides an output for each peak signal of the matched waveform.

The rate circuit 71 is also shown in FIG. 5 and includes flip-flop unit 144 connected to a monostable driver circuit 145 which includes suitable rate level control adjustable potentiometer 146. The output of circuit 145 is connected to the one input of an operational amplifier 147, the opposite reference input of which is connected to a driving circuit for the rate meter 7. Amplifier 147 has a feedback network 148 connected to the reference amplifier input, which also is connected to the base of driving transistor 149. The meter 7 is connected to a power supply in series with transistor 149 and a rate scale resistor 150, as shown. The conductivity of the transistor 149 thus controlled by the peak signal tugging of the monostable circuit 145 and thereby provides an output in accordance and the peak signal and therefore the heart rate.

The present invention although illustrated in a particular preferred use is generally applicable to virtually any pattern recognition analysis in which the pattern may be expressed in terms of an electrical signal or other signal which can be transduced to an electrical signal. Generally, the signal form is such that the significant data or information is present in some fixed relationship in various portions of the waveform. For example, the amplitude and/or phase relationship of the waveform contains the significant data or characteristic to be analyzed. This is in contrast for example to the general concept of frequency or spectral analysis where the particular signal at any given instant in the waveform signal is not directly indicative of the information. In such a waveform, however, the information might be processed to provide the necessary signal waveform.

The numeric diagnostic apparatus may, for example, be employed for measurement and analysis of various other repetitive or transient patterned electrical signals from the heart, brain and vascular system. Typical examples of a few of many of such applications which might be employed or analyzed include the following.

The numeric diagnostic apparatus might be employed to analyze information such as produced in a vector cardiometer, wherein sequence, direction magnitude and distribution of forces generated by the heart are presented as different forms of information derived from a single series of events related to a heart condition. The evaluation of this data is often helpful in evaluations of changes noted in an electrocardiogram and will even, at times, present valuable diagnostic information that is not appreciated on the standard electrocardiogram.

The instrument could be used to provide diagnosis of echoes from pulse high frequency sound waves used to locate and study the movements and dimensions of cardiac structures such as valve leaflets and chamber walls and the like as presently applied in electrocardiogram devices. The ultra-sound beam tracks the motion of the cardiac structures over a period of time, and thus it represents a time-motion study of the various cardiac structures and function. The electronic signals on this type of data generation can then be evaluated in reference to normal parameters that have been previously setup by logic filter structures as noted on previous reports on this new technique of numeric electrocardiometer studies, and the like.

In the cardiac catheterization procedures, catheters are placed in various parts of the venous arterial system for measurement of pressure, oxygen saturation, rate of change in the development of pressures in certain sections of the heat and vascular system, and recording of abnormal pulsations from various parts of the cardiovascular system. The graphic information or display of pressure pulses could be conveniently evaluated by the present invention.

In addition to various medical and human characteristics, other physical phenomena can, of course, be analyzed. For example, traffic assessment and control for mass transit, railroads, postal deliveries, or the like, seismic applications involved in oil exploration, earthquake detection/prediction and the like; dynamic vibration analysis such as structural analysis, vehicle or device stress testing, engine dynometer testing and the like. Other pattern recognition problems which are susceptible to analysis could include such diverse subjects as voice and/or finger "print" analysis, economic trends, demographic analysis.

Such a system is particularly applicable to applications such as the electrocardiographic, morphologic pattern recognition, vector cardiographic analysis, or seismic analysis for oil exploration.

Similarly, turbo jet engines, as constructed and after overhaul, are subjected to dynomometer tests including a test of vibration output. The defective part can often be located if frequency and energy is known as the engine is accelerated through various R.P.M. or energy outputs because various engine components function in several ratios to engine R.P.M. By expression of the system as a pattern recognition, depending on the engine mode and R.P.M., other applications would include pattern recognition through the use of electrical motion or acceleration transducers of the response of various dynamic loads such as a device undergoing a shake test, a bridge subjected to a dynamic traffic or wind load, and oil seismic studies in which sub-surface geologic structures respond to seismic energy waves as picked up by a phased array.

In applying the teaching of the invention to periodic or time dependent pattern recognition, the electrical data is either broken up into discrete time samples that may be sequentially analyzed or a continuing, uninterrupted periodic or aperiodic (synchronous or asynchronous) electrical signal is preprocessed to extract salient features such as power spectral density, frequency domain responses and the like for presentation in appropriate signal form. These features may in this manner be sequentially processed and classified.

Various modes of carrying out the invention are contemplated as being within the scope of the following claims, particularly pointing out and distinctly claiming the subject matter which is regarded as the invention.

I claim:

1. A diagnostic instrument having means to receive a waveform signal and adapted to drive a display means, comprising input means for sequentially sampling said waveform signal in time spaced samples and having digitizing means for digitizing said waveform samples into a series of time spaced digital samples which uniquely represent the characteristic of such waveform, storage means connected to said input means and having address means for recording said waveform samples as the series of time spaced digital signals, a preset referenced means defining a series of selected positions on the waveform as predetermined combinations of said sampled waveform characteristics and time intervals and having an output means, and address means connecting the storage means to the referenced means and providing an encoded indication output on said output means of normality and abnormality based on the waveform combination and the preset reference, said output means adapted to be connected to said display means and provide a display of said indication output for diagnosis of said waveform.

2. The diagnostic instrument of claim 1 wherein the reference means is a programmed logic array having a plurality of hardwired reference inputs establishing said reference signals and having a plurality of signal inputs connected to said storage means to input said samples.

3. In the diagnostic instrument of claim 2 wherein said storage means is a digital multibit memory unit in which each sample is stored as a combined time and sample data in a dual word format including a time word and a data word, said address means sequentially connecting the memory unit to the programmed logic array, each of said words including a plurality of multiple digital logic bits, said reference inputs includes corresponding multiple digital logic bits and including means for setting of the inputs whereby certain input bits are effectively made inoperative whereby the input is encoded to cover a range of said waveform, and said output signal thereby being coded to identify an abnormal state in a range of said waveform.

4. The diagnostic instrument of claim 2 including a second set of programmed logic arrays connected to the outputs of the first named set of logic arrays, said second set having an output generated in response to a selected difference in the setting of the second array and the inputs from the first array.

5. The instrument of claim 2 including visual display means connected to said programmed logic array to provide a visual readout of the encoded output.

6. The diagnostic instrument according to claim 1 wherein the input is adapted to receive plural discrete waveforms, and means for time division multiplexing said received waveforms and connecting the input means to the storage means for selective storage of said waveforms.

7. A numeric electrometer instrument having sensing electrode means for sensing a state to be monitored and producing a waveform signal and adapted to drive a display means, comprising input means for sequential sampling of said waveform in time spaced samples and having means converting each of the waveform samples into a corresponding series of unique digital numbers, a digital memory unit connected to said input means, said input means including address means directing such numbers in said digital memory unit for storage as a sequence of combined time and waveshape numbers, a programmed logic array having a corresponding reference waveform encoded as a series of preprogrammed time-amplitude number means one for each number of said waveform signals and defining abnormalities in the waveform signal as a class of combinations of a time period of the waveform and a waveshape for separately monitoring of said samples, said address means being connected to said memory unit and to said programmed logic array means for selectively impressing said stored numbers of said waveform signals on said logic array means for monitoring the state of each of said stored numbers, said programmed logic array including an output means producing an identifying coded output for each of said preprogrammed time-amplitude number means and which identifies a selected difference between numbers in the memory means and in the programmed logic array as an abnormality, said output means adapted to be connected to said display means and provide a display of said identifying coded output for diagnosis of said waveform.

8. The instrument of claim 7 wherein said sensing electrode means including a plurality of separate signal lead means, said programmed logic array includes a separate programmed logic array for each of said plurality of signal lead means, an instrumentation amplifier connected to each of said lead means to provide an amplified signal, an analog to digital converter, and a multiplexer connecting each of said plurality of lead means to said analog-to-digital converter for producing one of the digital numbers.

9. The instrument of claim 7 wherein said sensing electrode means includes a single signal lead electrode means for monitoring of different portions of a single integrated device, each portion generating unique waveform signals, said programmed logic array having a plurality of programmed logic arrays each of which is encoded to a different portion, and means to selectively enable the appropriate one of said plurality of logic arrays.

10. The instrument of claim 7 wherein the output means has means to display said digital numbers stored in said memory.

11. In the instrument of claim 7, having control means to detect a distinct point of said waveform, said address means for the memory unit being actuated by said control means to sequentially address the memory unit with the memory addresses assigned as time segments to the components of the wave, said reference waveform being assigned various time segment ranges within which certain significant amplitudes are checked, one of said logic arrays being connected to detect zero crossings of the waveform signal within the time segments to permit analysis of the various time characteristic of said waveform.

12. In the instrument of claim 11 having a controller connected to the input means and to the storage means and to the programmed logic arrays and having a sequence means with a plurality of output states for sequentially controlling the reading and storing of waveform samples and for transfer of the stored numbers to the programmed logic arrays, said controller having an analysis state output in which said address means is a resettable address means and is reset and operated to sequentially address the memory unit and apply stored memory words in a scanning sequence to the individual and corresponding time related program logic arrays, means responsive to a coded output within any assigned period of the waveform related to an abnormality to stop the scanning with the corresponding number applied to the program logic array producing an identifying output number, and means to restart the controller.

13. The instrument of claim 7 including a visual readout means connected to said output means and wherein said address means includes means for selective addressing and applying the stored waveform numbers to the programmed logic array as combined time and amplitude numbers and to the readout means for direct readout of the waveform numbers in the memory unit.

14. The instrument of claim 7 wherein said memory address means includes a resettable counter connected to said memory means and to said programmed logic array means said counter having a manually operable address selection means, and controller means connected to the input means and to the storage means and to the programmed logic arrays and having a sequence means with a plurality of output states and operable to actuate said address means to store data in said memory unit and then apply the stored numbers to the program logic array and to terminate the operation and condition the address selection means for operation.

15. The instrument of claim 14 having means to detect the distinct point in said waveform and actuate the counter such that the memory addresses are assigned as time segments to the components of the waveform, said logic arrays including preprogrammed time and zero amplitude numbers and thereby being encoded to detect zero crossings of the waveform signal impressed on the logic arrays within the time periods of the waveform to permit analysis of the various time characteristics of the waveform, and means to present an identifying code on said output means for said zero crossings.

16. In the instrument of claim 15 wherein said controller includes means monitoring the output means of the logic arrays and responsive to a zero crossing and to an abnormal condition within any assigned period of the waveform to stop the scanning with the corresponding identifying code presented, and means to restart the controller.

17. In the instrument of claim 7 having a scanning means to sequentially apply the numbers stored in the memory unit to the programmed logic arrays, logic means connected to each of said programmed logic arrays and responsive to creation of any of the unique numbers to terminate the scanning, said reference waveform being assigned various time segment ranges within which certain significant amplitudes are checked, one of said logic arrays includes a number encoded to define a particular repetitive time and amplitude waveshape in the waveform signal and connected to said logic means to terminate the scanning and permit analysis of the various time characteristic of the waveform signal.

18. In the instrument of claim 17 having a readout means connected to said programmed logic array and presenting the identifying code number in response to the stopping of the scanning, and means to restart the scanning means.

19. A diagnostic instrument having means to receive a waveform signal, comprising input means for sequentially sampling of said waveform signal in time spaced samples and having means for digitizing said waveform samples into a series of numbers which uniquely represent a waveshape characteristic of such waveform in a given time period, digital storage means to store said waveform numbers, each of said numbers being related to a particular waveshape characteristic of the waveform, a programmed means having a corresponding reference waveform encoded as a series of preprogrammed time-amplitude number means, one for each number of said waveform signal and defining abnormalities in the waveform signal as a class of combinations of a time period of the waveform and a waveshape for separately monitoring of said numbers, and address means to sequentially connect the storage means to the programmed means to introduce the stored numbers in sequence and generating an output signal in response to a selected difference in the stored number and the reference number in the programmed means, said output signal being encoded to identify the difference.

20. The diagnostic instrument of claim 19 wherein the programmed means includes a plurality of a programmed logic array chips each having a dual byte format including a multiple bit time byte and a multiple bit waveshape byte, each byte having selected unencoded bits whereby the byte defines a corresponding time and waveshape range.

* * * * *